(12) United States Patent
Gavney, Jr.

(10) Patent No.: US 7,814,603 B2
(45) Date of Patent: Oct. 19, 2010

(54) POWERED TOOTHBRUSH WITH POLISHING ELEMENTS

(76) Inventor: James A. Gavney, Jr., 725 Wildwood La., Palo Alto, CA (US) 94303

( * ) Notice: Subject to any disclaimer, the term of this patent is extended or adjusted under 35 U.S.C. 154(b) by 636 days.

(21) Appl. No.: 11/093,946

(22) Filed: Mar. 29, 2005

(65) Prior Publication Data

US 2005/0166343 A1 Aug. 4, 2005

Related U.S. Application Data

(63) Continuation-in-part of application No. 10/692,837, filed on Oct. 24, 2003, now Pat. No. 7,181,799, and a continuation-in-part of application No. 10/454,281, filed on Jun. 3, 2003, now Pat. No. 6,859,969, which is a continuation-in-part of application No. 09/330,704, filed on Jun. 11, 1999, now Pat. No. 6,319,332.

(60) Provisional application No. 60/439,317, filed on Jan. 10, 2003.

(51) Int. Cl.
*A61C 17/22* (2006.01)
(52) U.S. Cl. ............................ 15/110; 15/28
(58) Field of Classification Search .................. 15/106, 15/110–111, 114, 117, 167.1, 21.1, 22.1, 15/28, 180; 433/165–166
See application file for complete search history.

(56) References Cited

U.S. PATENT DOCUMENTS

| 34,109 | A | 1/1862 | Fenshaw et al. |
| 116,030 | A | 6/1871 | Devines |
| 116,346 | A | 6/1871 | O'Brian |
| 218,431 | A | 8/1879 | Dunham |
| 290,515 | A | 12/1883 | Voltz et al. |
| 305,735 | A | 9/1884 | Leeson et al. |
| 411,910 | A | 10/1889 | Van Home |
| 620,151 | A | 2/1899 | Emsa-Works et al. |
| 742,639 | A | 10/1903 | Harlan |
| 907,842 | A | 12/1908 | Meuzies |

(Continued)

FOREIGN PATENT DOCUMENTS

DE 31 14 507 A1 3/1983

(Continued)

OTHER PUBLICATIONS

"A new high-performance manual toothbrush" Supported by the Colgate-Palmolive Company, 2004 Medical World Business Press, Inc.

(Continued)

*Primary Examiner*—Laura C Guidotti
(74) *Attorney, Agent, or Firm*—Jag Patent Services LLC; James A. Gavney, Jr.

(57) ABSTRACT

An electric toothbrush system or toothbrush head is disclosed. The cleaning head in accordance with the embodiments of the invention includes at least one movable section that is configured to rotate, vibrate, oscillate or a combination thereof and has at least one prophy-cup structure and/or one or more polishing elements protruding therefrom. Preferably, the cleaning head also includes bristle tufts. The cleaning head can be configured to detachably couple to a motorized handle. The motorized handle can include a rechargeable battery that is configured to couple to a recharging station.

12 Claims, 7 Drawing Sheets

U.S. PATENT DOCUMENTS

| | | | |
|---|---|---|---|
| 915,251 A | 3/1909 | Vanderslice | |
| 1,006,630 A | 10/1911 | Clarke | |
| 1,128,139 A | 2/1915 | Hoffman | |
| 1,142,698 A | 6/1915 | Grove at al. | |
| 1,188,823 A | 6/1916 | Plank | |
| 1,191,556 A | 7/1916 | Blake | |
| 1,268,544 A | 6/1918 | Cates | |
| 1,297,272 A | 3/1919 | Strang et al. | |
| 1,405,279 A | 1/1922 | Cassedy | |
| 1,500,274 A | 7/1924 | Scarling | |
| 1,526,267 A | 2/1925 | Dessau | |
| 1,578,074 A | 3/1926 | Chandler | |
| 1,588,785 A | 6/1926 | Van Sant | |
| 1,598,224 A | 8/1926 | Van Sant | |
| 1,705,249 A | 3/1929 | Henry | |
| 1,707,118 A | 3/1929 | Goldberg | |
| 1,720,017 A | 7/1929 | Touchstone | |
| 1,766,529 A | 6/1930 | Peirson | |
| 1,833,555 A | 11/1931 | Bell et al. | |
| 1,852,480 A | 4/1932 | Ruetz | |
| 1,868,893 A | 7/1932 | Gentle | |
| 1,907,286 A * | 5/1933 | Chott | 15/110 |
| 1,910,414 A | 5/1933 | Varga | |
| 1,924,152 A | 8/1933 | Coney et al. | 15/167 |
| 1,965,009 A | 7/1934 | Stevens | 15/188 |
| 1,993,662 A | 3/1935 | Green | 15/110 |
| 2,008,636 A | 7/1935 | Brynan | 91/67.4 |
| 2,039,278 A * | 5/1936 | Blanchard | 15/188 |
| 2,042,239 A | 5/1936 | Planding | 15/110 |
| 2,059,914 A | 11/1936 | Rosenberg | 15/110 |
| 2,088,839 A | 8/1937 | Coney et al. | 15/188 |
| 2,117,174 A | 5/1938 | Jones | 15/110 |
| 2,129,082 A | 9/1938 | Byrer | 128/62 |
| 2,139,245 A | 12/1938 | Ogden | 128/62 |
| 2,154,846 A | 4/1939 | Heymann et al. | 128/62 |
| 2,219,753 A | 10/1940 | Seguin | 15/188 |
| 2,226,145 A | 12/1940 | Smith | 15/29 |
| 2,244,699 A | 6/1941 | Hosey | 15/188 |
| 2,279,355 A | 4/1942 | Wilensky | 15/110 |
| 2,312,828 A | 3/1943 | Adarnsson | 15/167 |
| 2,321,333 A | 6/1943 | Terry | 15/135 |
| 2,334,796 A | 11/1943 | Steinmetz et al. | 15/121 |
| 2,364,205 A * | 12/1944 | Fuller | 601/141 |
| 2,443,461 A | 6/1948 | Kempster | 15/188 |
| 2,516,491 A | 7/1950 | Swastek | 15/188 |
| 2,518,765 A | 8/1950 | Ecker | 15/115 |
| 2,534,086 A | 12/1950 | Vosbikian et al. | 15/245 |
| 2,545,814 A | 3/1951 | Kempster | 15/188 |
| 2,637,870 A | 5/1953 | Cohen | 15/188 |
| 2,702,914 A | 3/1955 | Kittle et al. | 15/114 |
| 2,757,668 A | 8/1956 | Meyer-Saladin | 128/173.1 |
| 2,815,601 A | 12/1957 | Hough, Jr. | 41/5.5 |
| 2,875,458 A | 3/1959 | Tsuda | 15/22 |
| 2,884,151 A | 4/1959 | Biederman | 215/41 |
| 2,987,742 A | 6/1961 | Kittle et al. | 15/114 |
| 3,103,027 A | 9/1963 | Birch | 15/110 |
| 3,110,052 A | 11/1963 | Whitman | 15/117 |
| 3,133,546 A | 5/1964 | Dent | 132/120 |
| 3,181,193 A | 5/1965 | Nobles et al. | 15/114 |
| 3,195,537 A | 7/1965 | Blasi | 128/56 |
| 3,196,299 A * | 7/1965 | Kott | 310/81 |
| 3,230,562 A | 1/1966 | Birch | 15/110 |
| 3,231,925 A | 2/1966 | Conder | 15/605 |
| 3,261,354 A | 7/1966 | Shpuntoff | 128/173 |
| 3,359,588 A | 12/1967 | Kobler | 15/110 |
| 3,400,417 A | 9/1968 | Moret | 15/22 |
| 3,491,396 A | 1/1970 | Eannarino et al. | 15/104.94 |
| 3,553,759 A | 1/1971 | Kramer et al. | 15/110 |
| 3,563,233 A | 2/1971 | Bodine | 128/36 |
| 3,570,726 A | 3/1971 | Pomodoro | 222/546 |
| 3,641,610 A | 2/1972 | Lewis, Jr. | 15/114 |
| 3,939,522 A | 2/1976 | Shimizu | 15/244 R |
| 3,969,783 A | 7/1976 | Shipman | 15/250.04 |
| 3,977,084 A | 8/1976 | Sloan | 32/59 |
| 3,992,747 A | 11/1976 | Hufton | 15/321 |
| 4,090,647 A | 5/1978 | Dunning | 222/543 |
| 4,115,893 A | 9/1978 | Nakata et al. | 15/110 |
| 4,128,910 A | 12/1978 | Nakata et al. | 15/110 |
| 4,167,794 A | 9/1979 | Pomeroy | 15/188 |
| 4,277,862 A | 7/1981 | Weideman | 15/110 |
| 4,428,091 A | 1/1984 | Janssen | 15/167 A |
| 4,458,374 A | 7/1984 | Hukuba | 15/22 R |
| 4,573,920 A | 3/1986 | d'Argembeau | 433/141 |
| 4,585,416 A | 4/1986 | DeNiro et al. | 433/140 |
| 4,610,043 A | 9/1986 | Vezjak | 15/111 |
| 4,691,405 A | 9/1987 | Reed | 15/201 |
| 4,763,380 A | 8/1988 | Sandvick | 15/160 |
| 4,812,070 A | 3/1989 | Marty | 401/289 |
| 4,827,551 A | 5/1989 | Maser et al. | 15/24 |
| 4,866,806 A | 9/1989 | Bedford | 15/104.94 |
| 4,887,924 A | 12/1989 | Green | 401/261 |
| 4,913,133 A | 4/1990 | Tichy | 128/62 |
| 4,929,180 A | 5/1990 | Moreschini | 433/166 |
| 5,005,246 A | 4/1991 | Yen-Hui | 15/111 |
| 5,032,082 A | 7/1991 | Herrera | 433/141 |
| 5,040,260 A | 8/1991 | Michaels | 15/167.1 |
| D326,019 S | 5/1992 | Spangler et al. | D4/118 |
| 5,211,494 A | 5/1993 | Baijnath | 401/28 |
| 5,226,197 A | 7/1993 | Nack et al. | 15/111 |
| 5,249,327 A | 10/1993 | Hing | 15/104.94 |
| 5,283,921 A | 2/1994 | Ng | 15/22.1 |
| 5,289,605 A | 3/1994 | Armbruster | 15/97.1 |
| 5,335,389 A | 8/1994 | Curtis et al. | 15/167.1 |
| 5,341,537 A | 8/1994 | Curtis et al. | 15/167.1 |
| 5,438,726 A | 8/1995 | Leite | 15/105 |
| 5,491,863 A | 2/1996 | Dunn | 15/106 |
| 5,528,793 A | 6/1996 | Schbot | 15/245 |
| 5,535,474 A | 7/1996 | Salazar | 15/110 |
| 5,584,690 A | 12/1996 | Maassarani | 433/125 |
| 5,604,951 A | 2/1997 | Shipp | 15/167.1 |
| 5,628,082 A | 5/1997 | Moskovich | 15/110 |
| 5,669,097 A | 9/1997 | Klinkhammer | 15/167.1 |
| 5,689,850 A | 11/1997 | Shekalim | 15/22.1 |
| 5,711,759 A | 1/1998 | Smith et al. | 601/139 |
| 5,735,011 A | 4/1998 | Asher | 15/167.1 |
| 5,775,905 A * | 7/1998 | Weissenfluh et al. | 433/166 |
| 5,799,353 A | 9/1998 | Oishi et al. | 15/167.1 |
| 5,802,656 A | 9/1998 | Dawson et al. | 15/110 |
| 5,806,127 A | 9/1998 | Samoil et al. | 15/104.94 |
| 5,810,856 A | 9/1998 | Tveras | 606/161 |
| D402,116 S | 12/1998 | Magloff et al. | D4/104 |
| D403,510 S | 1/1999 | Menke et al. | D4/104 |
| 5,896,614 A | 4/1999 | Flewitt | 15/167.1 |
| 5,930,860 A | 8/1999 | Shipp | 15/110 |
| 5,966,771 A | 10/1999 | Stroud | 15/117 |
| 5,970,564 A | 10/1999 | Inns et al. | 15/201 |
| 5,980,542 A | 11/1999 | Saldivar | 606/161 |
| 5,991,959 A | 11/1999 | Raven et al. | 15/201 |
| 6,021,541 A | 2/2000 | Mori et al. | 15/167.1 |
| 6,032,313 A | 3/2000 | Tsang | 15/22.1 |
| 6,032,322 A | 3/2000 | Forsline | 15/245.1 |
| 6,041,467 A | 3/2000 | Roberts et al. | 15/167.1 |
| D422,143 S | 4/2000 | Beals et al. | D4/104 |
| 6,044,514 A | 4/2000 | Kaneda et al. | 15/167.1 |
| D424,808 S | 5/2000 | Beals et al. | D4/104 |
| D425,306 S | 5/2000 | Beals et al. | D4/104 |
| 6,065,890 A | 5/2000 | Weitz | 401/146 |
| 6,067,684 A | 5/2000 | Kweon | 15/167.1 |
| 6,077,360 A | 6/2000 | Takashima | 134/6 |
| 6,088,869 A | 7/2000 | Kaneda et al. | 15/167.1 |
| 6,099,309 A | 8/2000 | Cardarelli | 433/125 |
| 6,108,854 A | 8/2000 | Dingert | 15/188 |
| 6,115,871 A | 9/2000 | Royer | 15/167.2 |
| 6,126,533 A | 10/2000 | Johnson et al. | 451/527 |

| | | | |
|---|---|---|---|
| 6,151,745 A | 11/2000 | Roberts et al. ............. 15/167.1 |
| 6,151,746 A | 11/2000 | Lewis, Jr. .................... 15/187 |
| 6,168,434 B1 | 1/2001 | Bohm-Van Diggelen .... 433/141 |
| 6,182,323 B1 | 2/2001 | Bahten .................... 12/230.16 |
| 6,182,365 B1 | 2/2001 | Tseng et al. ................. 30/34.2 |
| 6,190,367 B1 | 2/2001 | Hall ........................... 604/290 |
| 6,219,874 B1 | 4/2001 | van Gelder et al. ........ 15/167.1 |
| 6,240,590 B1 | 6/2001 | Nesbit ........................ 15/210.1 |
| 6,245,032 B1 | 6/2001 | Sauer et al. ................. 601/162 |
| 6,254,390 B1 | 7/2001 | Wagner ...................... 433/216 |
| 6,272,713 B1 | 8/2001 | Lotwin .................. 15/104.061 |
| 6,276,021 B1 | 8/2001 | Hohlbein ................... 15/167.1 |
| 6,299,508 B1 | 10/2001 | Gagliardi et al. ............. 451/28 |
| 6,311,360 B1 | 11/2001 | Lanvers ...................... 15/191.1 |
| 6,319,332 B1 | 11/2001 | Gavney, Jr. et al. ............ 134/6 |
| 6,347,425 B1 * | 2/2002 | Fattori et al. ................. 15/22.1 |
| 6,349,442 B1 | 2/2002 | Cohen et al. ................. 15/22.1 |
| 6,374,448 B2 * | 4/2002 | Seifert ......................... 15/110 |
| 6,421,867 B1 | 7/2002 | Weihrauch .................... 15/28 |
| 6,446,295 B1 | 9/2002 | Calabrese ...................... 15/28 |
| 6,463,619 B2 | 10/2002 | Gavney, Jr. .................. 15/117 |
| 6,510,575 B2 | 1/2003 | Calabrese ................... 15/22.1 |
| 6,513,182 B1 | 2/2003 | Calabrese et al. ............. 15/110 |
| 6,571,417 B1 | 6/2003 | Gavney, Jr. et al. ........... 15/117 |
| 6,647,585 B1 | 11/2003 | Robinson ..................... 15/322 |
| D483,184 S | 12/2003 | Geiberger et al. ............ D4/104 |
| 6,658,688 B2 | 12/2003 | Gavney, Jr. .................. 15/117 |
| 6,658,692 B2 | 12/2003 | Lenkiewicz et al. ........... 15/320 |
| 6,668,418 B2 | 12/2003 | Bastien ........................ 15/245 |
| 6,725,493 B2 | 4/2004 | Calabrese et al. ............. 15/110 |
| 6,751,823 B2 | 6/2004 | Biro et al. ................... 15/22.1 |
| 6,813,793 B2 | 11/2004 | Eliav et al. ................... 15/22.2 |
| 6,817,054 B2 | 11/2004 | Moskovich et al. ........ 15/167.1 |
| 6,820,299 B2 | 11/2004 | Gavney, Jr. .................. 15/117 |
| 6,820,300 B2 | 11/2004 | Gavney, Jr. .................. 15/117 |
| 6,859,969 B2 | 3/2005 | Gavney, Jr. .................. 15/117 |
| 6,865,767 B1 | 3/2005 | Gavney, Jr. .................. 15/114 |
| 6,892,412 B2 | 5/2005 | Gatzemeyer et al. ......... 15/22.2 |
| 6,938,507 B2 | 9/2005 | Fisher ........................ 15/22.1 |
| 2001/0039689 A1 | 11/2001 | Gavney, Jr. .................. 15/117 |
| 2002/0124337 A1 | 9/2002 | Calabrese et al. ............. 15/110 |
| 2003/0033680 A1 | 2/2003 | Davies et al. ................ 15/22.1 |
| 2003/0033682 A1 | 2/2003 | Davies et al. ................. 15/110 |
| 2003/0140437 A1 * | 7/2003 | Eliav et al. ................... 15/22.2 |
| 2003/0196283 A1 | 10/2003 | Eliav et al. ................... 15/22.1 |
| 2004/0010869 A1 | 1/2004 | Fattori et al. ................. 15/22.1 |
| 2004/0045105 A1 | 3/2004 | Eliav et al. ................... 15/22.1 |
| 2004/0060132 A1 | 4/2004 | Gatzemeyer et al. ......... 15/22.1 |
| 2004/0060133 A1 | 4/2004 | Eliav et al. ................... 15/22.1 |
| 2004/0060135 A1 | 4/2004 | Gatzemeyer et al. ......... 15/22.1 |
| 2004/0060136 A1 | 4/2004 | Gatzemeyer et al. ......... 15/22.1 |
| 2004/0060137 A1 | 4/2004 | Eliav .......................... 15/22.1 |
| 2004/0154112 A1 | 8/2004 | Braun et al. ................. 15/22.1 |
| 2004/0200016 A1 | 10/2004 | Chan et al. ................... 15/22.1 |
| 2005/0000048 A1 | 1/2005 | Hohlbein ...................... 15/110 |
| 2005/0049155 A1 | 3/2005 | Gavney, Jr. et al. ......... 510/108 |
| 2005/0060822 A1 | 3/2005 | Chenvainu et al. |
| 2005/0166342 A1 | 8/2005 | Hohlbein ..................... 15/110 |

FOREIGN PATENT DOCUMENTS

| | | |
|---|---|---|
| DE | 298 16 488 U1 | 1/1999 |
| DE | 199 57 639 A1 | 6/2001 |
| FR | 2 636 818 | 3/1990 |
| FR | 2 793 136 | 11/2000 |
| GB | 2 040 161 A | 8/1980 |
| JP | 9-140456 | 3/1997 |
| WO | WO 96/20654 | 7/1996 |
| WO | WO 96/28994 | 9/1996 |
| WO | WO 98/18364 | 5/1998 |
| WO | WO 98/22000 | 5/1998 |
| WO | WO 01/01817 A1 | 1/2001 |
| WO | WO 01/21036 A1 | 3/2001 |
| WO | WO 03/030680 A1 | 4/2003 |
| WO | WO 03/043459 A2 | 5/2003 |
| WO | WO 2004/041023 A2 | 5/2004 |
| WO | WO 2004/064573 A1 | 8/2004 |

OTHER PUBLICATIONS

The Gillette Company, 2004 Annual Report and 2005 Proxy Statement.

* cited by examiner

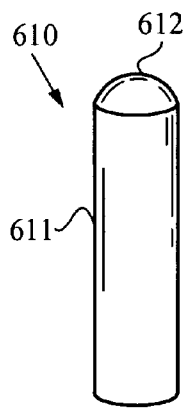
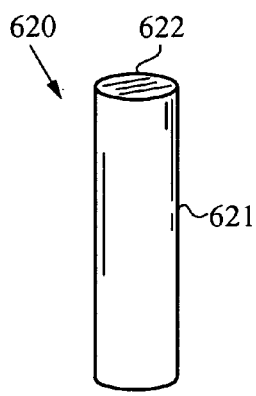
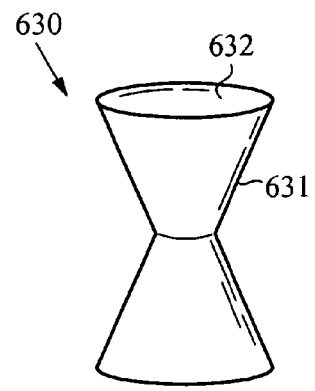
*Fig. 6A*   *Fig. 6B*   *Fig. 6C*
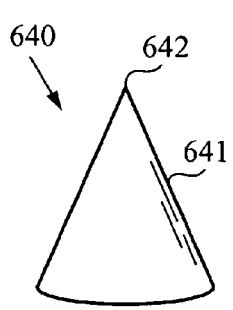
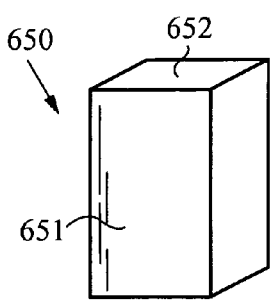
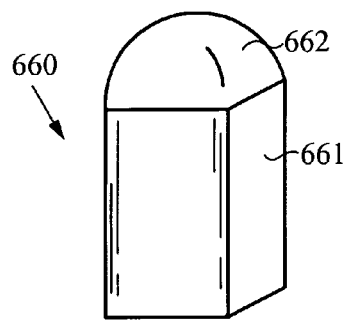
*Fig. 6D*   *Fig. 6E*   *Fig. 6F*
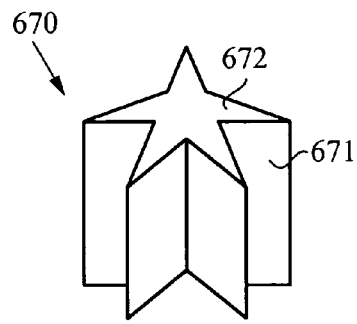
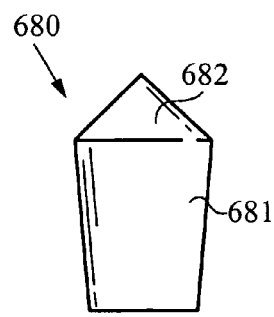
*Fig. 6G*   *Fig. 6H*

POWERED TOOTHBRUSH WITH POLISHING ELEMENTS

RELATED APPLICATION(S)

This application is a Continuation-in-part of the application Ser. No. 10/692,837 filed Oct. 24, 2003 now U.S. Pat. No. 7,181,799, and titled "ORAL-CARE DEVICE AND SYSTEM", and the application Ser. No. 10/454, 281 filed Jun. 3, 2003 now U.S. Pat. No. 6,859,969, and titled "MULTI-DIRECTIONAL WIPING ELEMENTS AND DEVICE USING THE SAME", which is a Continuation-in-part of application Ser. No. 09/330,704 filed Jun. 11, 1999, and titled "SQUEEGEE DEVICE AND SYSTEM", now U.S. Pat. No. 6,319,332. The Co-pending application Ser. No. 10/692,837 filed Sep. 24, 2003, and titled "ORAL-CARE DEVICE AND SYSTEM", and the Co-pending application Ser. No. 10/454, 281 filed Jun. 3, 2003, and titled "MULTI-DIRECTIONAL WIPING ELEMENTS AND DEVICE USING THE SAME" both claim priority under 35 U.S.C. §119 (e) from the U.S. Provisional Patent Application Ser. No. 60/439,317, filed Jan. 10, 2003, and titled "TOOTHBRUSH". The Co-pending application Ser. No. 10/692,837 filed Sep. 24, 2003, and titled "ORAL-CARE DEVICE AND SYSTEM", the Co-pending application Ser. No. 10/454, 281 filed Jun. 3, 2003, and titled "MULTI-DIRECTIONAL WIPING ELEMENTS AND DEVICE USING THE SAME", the application Ser. No. 09/330,704 filed Jun. 11, 1999, and titled "SQUEEGEE DEVICE AND SYSTEM", now U.S. Pat. No. 6,319,332 and the Provisional Patent Application Ser. No. 60/439,317 filed Jan. 10, 2003, and titled "TOOTHBRUSH", are all hereby incorporated by reference.

FIELD OF THE INVENTION

This invention relates to oral-care devices. More specifically this invention relates to oral care devices with prophy-cup or polishing elements and bristle fields.

BACKGROUND

There are a number of different systems and devices available for cleaning teeth and gums. A number of these available systems and devices are inefficient at cleaning teeth and gums and require multiple pass scrubbing with oral cleaning agents, such as tooth pastes or gels, to effectively clean teeth and gums. Typically, toothbrushes do not efficiently apply the oral cleaning agents to teeth and gums and can be abrasive, causing loss of healthy gum tissue and/or damage to teeth. Further, toothbrushes can require a high degree of technique and/or dexterity to be used effectively for cleaning teeth and gums.

What is needed is a dentition cleaning system and device that can efficiently apply oral cleaning agents to teeth and gums and that can clean teeth and gums without a high degree of technique or dexterity. Further, what is needed is a dentition cleaning system and device that is less abrasive to teeth and gums than a conventional bristle toothbrush and that can polish teeth while cleaning under the gum-line.

SUMMARY OF THE INVENTION

The present invention is to an electric toothbrush system or toothbrush head that can be detachably coupled to a motorized handle. The toothbrush head includes at least one movable section that is configured to rotate, vibrate and/or oscillate. The movable section includes at least one prophy-cup structure and/or one or more polishing elements and bristle tufts protruding therefrom.

In accordance with the embodiments of the invention the prophy-cup structure includes at least one curved squeegee that encircles a region, a plurality of curved squeegee segments or a combination thereof. The bristle tufts are either encircled by portions of the prophy-cup structure, surround portions of the prophy-cup structure, surround a nodular polishing element, are located between nodular polishing elements or any combination thereof. In accordance with a preferred embodiment of the invention, a portion of the bristles surrounds portions of a prophy-cup structure, wherein at least a portion of the bristle protrude with bristle tips that extend from the movable section a distance that is equal to or greater than a distance of the polishing edge or wiping edges of the prophy-cup structure.

In accordance with further embodiments of the invention an electric toothbrush system or toothbrush head includes nodular polishing elements, which are resilient protrusions with any number of different geometries such as described below and further described in U.S. Pat. No. 6,859,969, titled "MULTI-DIRECTIONAL WIPING ELEMENTS AND DEVICE USING THE SAME", the contents of which are hereby incorporated by reference.

BRIEF DESCRIPTION OF THE FIGURES

FIGS. 6A-H show nodule polishing elements, in accordance with the embodiments of the invention.

DETAILED DESCRIPTION

Polishing elements and/or portions thereof, in accordance with the embodiments of the present invention, are preferably configured to clean surfaces, apply materials to surfaces and/or otherwise treat surfaces. In accordance with a preferred embodiment of the invention, polishing elements are configured to treat dentition. Polishing elements, utilized in the present invention, can be formed from any number of different materials, but are preferably formed from a resilient polymeric material such as silicon, latex, rubber, polyurethane or a combination thereof. Preferably, polishing elements, or a portion thereof, are formed from a material, or materials, that can be molded and that result in squeegees with hardness values in a range of 10 to 100 Shores A, as defined in the D2240-00 Standard Test Method for Rubber Property-Durometer Hardness, published by the American Society for Testing Materials, the contents of which are hereby incorporated by reference. Also, top wiping edges, side wiping edges and walls of the polishing elements can be shaped or contoured in any number of ways. For example, top and/or side wiping squeegee edges are corrugated, rounded, angled and/or pointed, and walls are curved, textured and/or tapered. Further, polishing elements and/or portions thereof can include an abrasive material. Methods and materials for making molded abrasive structures are described in U.S. Pat. No. 6,126,533, and titled "MOLDED ABRASIVE BRUSH", the contents of which are hereby incorporated by reference.

It is understood that polishing element geometries, configurations, physical properties and materials used to form polishing elements described above apply to all of the examples herein. Further, while direct reference to polishing elements are described as being used in oral-care systems and devices, it will be understood by one skilled in the art that any number of different applications are within the scope of the invention.

Figure 1A:
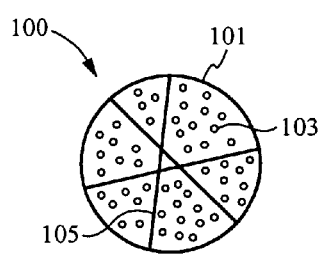
FIGS. 1A-1F show schematic top views of movable sections of cleaning head configurations that include prophy-cup structures, in accordance with the embodiments of the invention.
Figure 1B:
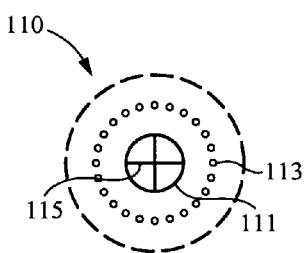
Figure 1C:
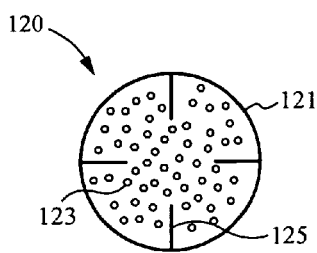
Figure 1D:
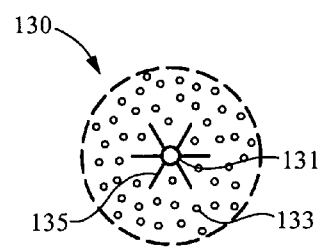
Figure 1E:
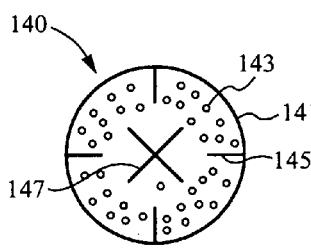
Figure 1F:
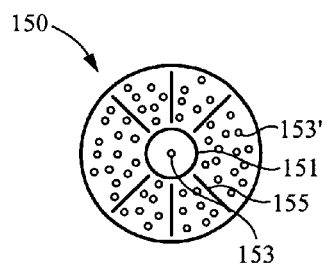

FIGS. 1A-1$f$ show schematic top views of movable sections of cleaning heads with polishing elements and bristle fields, in accordance with the embodiments of the invention. FIG. 1A shows a movable section 100 that includes a continuous squeegee 101 that encircles a plurality of bristle tufts 103 and a plurality of intersecting squeegee segments 105; FIG. 1B shows a movable section 110 that includes a continuous squeegee 111, a plurality of bristle tufts 113 that surround the continuous squeegee 111 and a plurality of intersecting squeegee segments 115; FIG. 1C shows a movable section 120 that includes a continuous squeegee 121 that encircles a plurality of bristle tufts 123 and includes a plurality squeegee fins 125 that extend from an inner wall of the continuous squeegee 121; FIG. 1D shows a movable section 130 that includes a continuous squeegee 131 surrounded by a plurality of bristle tufts 133 and includes a plurality squeegee fins 135 that extend from an outer wall of the continuous squeegee 131; FIG. 1E shows a movable section 140 that includes a continuous squeegee 141 that encircles a plurality of bristle tufts 143 and intersecting squeegee segments 147 and includes a plurality of squeegee fins 145 that extend from an inner wall of the continuous squeegee 141; FIG. 1F shows a movable section 150 that includes a continuous squeegee 151 that encircle one or more bristle tufts 153 and is surrounded by bristle tufts 153', and includes a plurality of squeegee segments 155 that extend radially outward on the movable section. Other squeegee configurations that are used alone or in combination with bristle tufts for oral-care devices and systems are described in the application Ser. No. 10/692, 837, filed Sep. 24, 2003, and titled "ORAL-CARE DEVICE AND SYSTEM", and the U.S. Pat. No. 6,859,969, titled "MULTI-DIRECTIONAL WIPING ELEMENTS AND DEVICE USING THE SAME", the contents of which are both hereby incorporated by reference.

While FIGS. 1A-1F are described as having bristle tufts, it will be clear to one skilled in the art from the description below that the cleaning head configurations described above can include, in place of bristle tufts or in addition to bristle tufts, nodule polishing elements, such as those described with reference to FIGS. 6A-H and FIGS. 7A-G below. Also, squeegee walls and edges can be shaped or contoured in any number of different ways, such as described with reference to FIGS. 5A-5F below.

Figure 2A:
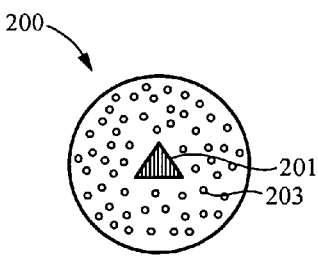
FIGS. 2A-2B show schematic top views of movable sections of cleaning head configurations that include nodule polishing elements and bristle tufts, in accordance with further embodiments of the invention.
Figure 2B:
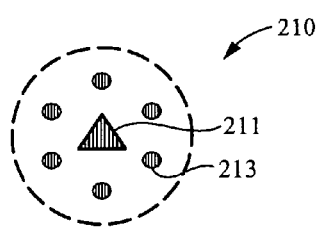

FIGS. 2A-2B show schematic top views of movable sections of cleaning head configurations with nodule polishing elements and bristle tufts, in accordance with further embodiments of the invention. FIG. 2A shows a movable section 200 with a triangular-shaped polishing nodule 201 that is surrounded by a plurality of bristle tufts 203; and FIG. 2B shows a movable section 210 with triangular-shaped polishing nodule 211 with a plurality of conical-shaped polishing nodules and/or bristle tufts 213 that surround the triangular-shaped polishing nodule 211. Again, nodule shaped polishing elements in accordance with the embodiments of the invention have polishing tips and walls that are shaped or contoured in any number of different ways, such as those described with reference to FIGS. 6A-H and FIGS. 7A-G below.

Figure 3A:
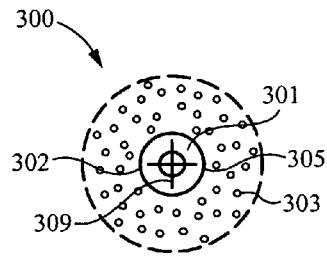
FIGS. 3A-3B show a top schematic view and a side cross-sectional view of cleaning head configurations with a cup-shaped polishing element, in accordance with further embodiments of the invention.
Figure 3B:
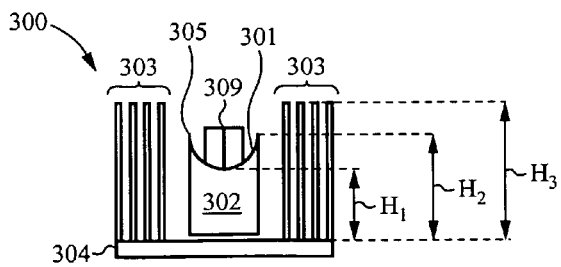

FIGS. 3A-3B show a top schematic view and a side cross-sectional view, respectfully, of movable section 300 of a cleaning head, in accordance with the embodiments of the invention. The movable section 300 includes a cup-shaped polishing element 302 that is surrounded by a plurality of bristle tufts 303. The cup-shaped polishing element 302 has a concave surface 301 that provide a continuous polishing edge 305. The bristle tufts 303 can protrude from a movable support surface 304 to a height $H_1$ equal with the bottom portion of the concave surface 301 of the cup-shaped polishing element 302, to a height $H_2$ that is equal to that of the polishing edge 305 of the cup-shaped polishing element 302, to a height $H_3$ that is greater that the polishing edge 305 of the cup-shaped polishing element 302, heights in between $H_1$, $H_2$ and $H_3$ or any suitable range of heights. Preferably, at least a portion of the bristle tufts 303 protrude from the movable support surface 304 to a distance that is greater than the polishing edge 305 of the cup-shaped polishing element 302.

Still referring to FIGS. 3A-3B, in accordance with further embodiments of the invention, the cup-shaped polishing element 302 has a second polishing 309 protruding from the surface 301. The second polishing structure can be a squeegee configuration that can include intersecting squeegee segments that from a cross-shaped polishing edge as shown, or can include a squeegee configuration with any number of different geometries. Squeegee configuration with intersection squeegee segments are further described in U.S. Pat. No. 6,859,969, titled "MULTI-DIRECTIONAL WIPING ELEMENTS AND DEVICE USING THE SAME", referenced previously.

Further, the cup-shaped polishing element 302 can include secondary structure that includes nodules and/or bristles that protrude from the surface 309. Polishing elements that includes secondary structures, such as squeegees, nodules, bristles and combinations thereof are further described in U.S. Pat. No. 6,865,767, titled "DEVICE WITH MULTI-STRUCTURAL CONTACT ELEMENTS", referenced previously.

Figure 4A:
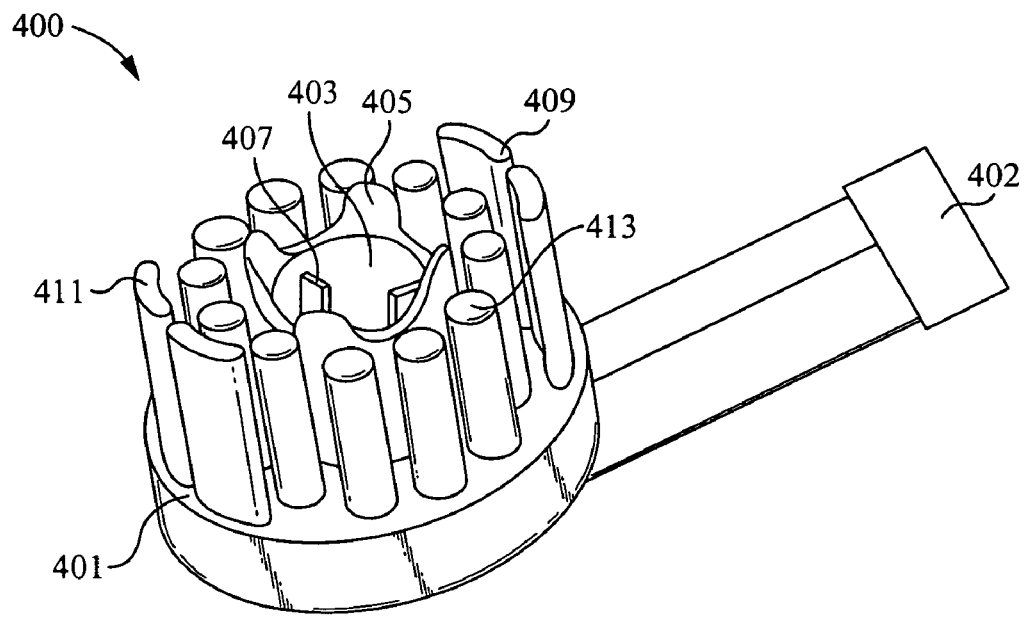
FIGS. 4A-4D show perspective views of cleaning head configurations with prophy-cup polishing elements and bristle tufts, in accordance with further embodiments of the invention.

FIGS. 4A-4D show perspective views of cleaning head configurations with prophy-cup polishing elements, bristle tufts and/or nodule polishing elements, in accordance with further embodiments of the invention. Referring to FIG. 4A, the cleaning head 400 includes a prophy-cup polishing element 403 protruding from a movable support 401. The prophy-cup polishing element 403 has corrugated or contoured polishing edge 405 and a plurality of wiping fins 407 extending inward from an inner wall of the prophy-cup polishing element 403. The cleaning head 400 also includes a plurality of bristle tufts and/or nodule polishing elements 413 protruding from the movable support 401 and surrounding the prophy-cup polishing element 403. The cleaning head 400 can also include curved squeegee polishing elements or curved bristle tufts 409 and 411.

Figure 4B:
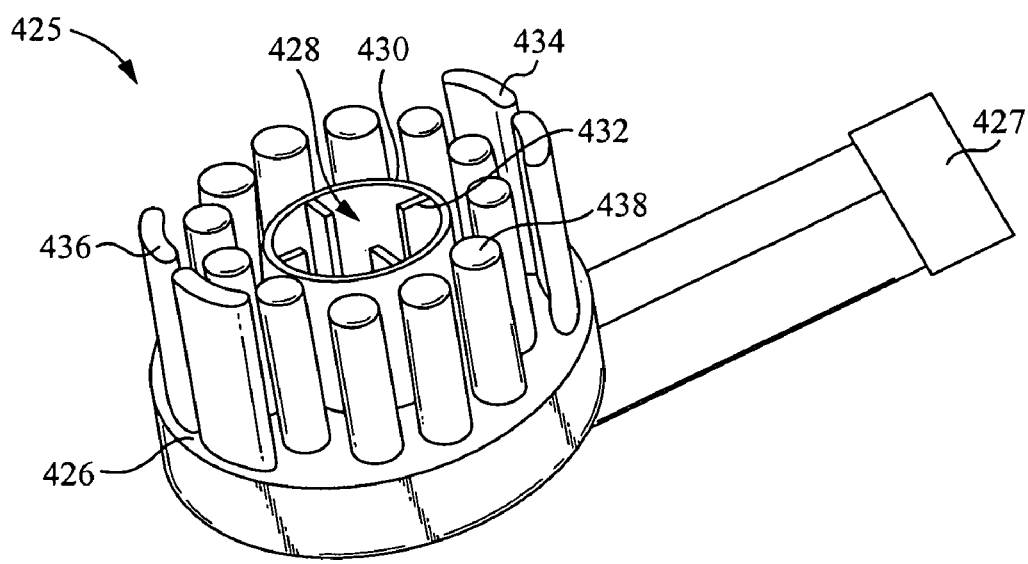
Figure 4C:
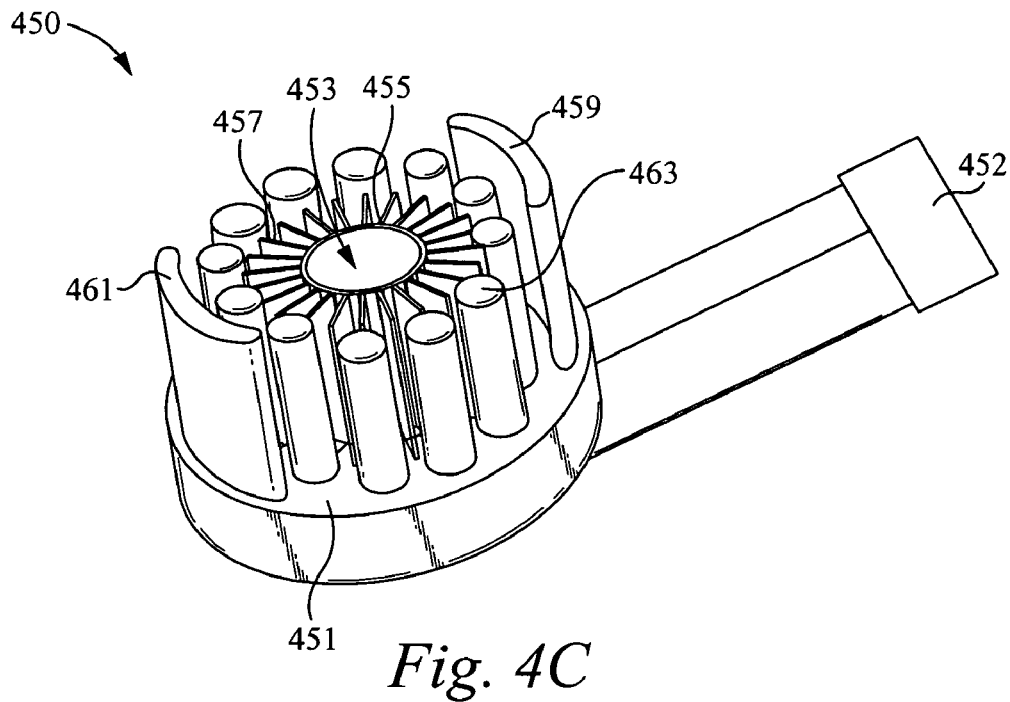

FIG. 4B shows a cleaning head 425 that includes a prophy-cup polishing element 428 protruding from a movable support 426. The prophy-cup polishing element 428 has a continuous polishing edge 430 and a plurality of wiping fins 432 extending inward from an inner wall of the prophy-cup polishing element 428. The cleaning head 425 also includes a plurality of bristle tufts and/or nodule polishing elements 438 protruding from the movable support 426 and surrounding prophy-cup polishing element 428. The cleaning head 425 can also include curved squeegee polishing elements or curved bristle tufts 434 and 436. FIG. 4C shows a cleaning head 450 that includes a prophy-cup polishing element 453 protruding from a movable support 451. The prophy-cup polishing element 453 has a continuous polishing edge 455 and a plurality of wiping fins 457 that extend outward from an outer wall of the prophy-cup polishing element 453. The cleaning head 450 also includes a plurality of bristle tufts and/or nodule polishing elements 463 protruding from the movable support 451 and surrounding prophy-cup polishing element 453. The cleaning head 450 can also include curved squeegee polishing elements or curved bristle tufts 459 and 461.

Figure 4D:
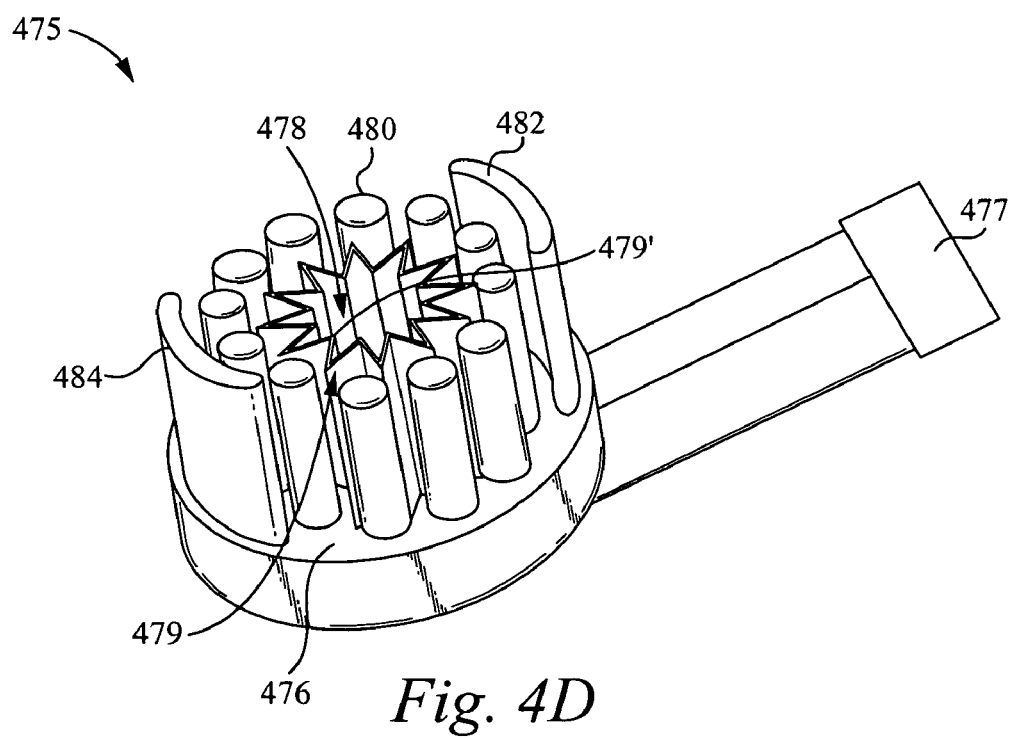

FIG. 4D shows a cleaning head 475 that includes a prophy-cup polishing element 478 protruding from a movable support 476. The prophy-cup polishing element 478 has corrugated or angled walls 479 and 479' that provides a zig zag-like top wiping edge. The cleaning head 475 also includes a plurality of bristle tufts and/or nodule polishing elements 480 protruding from the movable support 476 and surrounding prophy-cup polishing element 478. The cleaning head 478 can also include curved squeegee polishing elements or curved bristle tufts 482 and 484. Each of the cleaning heads 400, 425, 450 and 475 can include an attachment means 402, 427, 452 and 477, respectfully, for detachably coupling the cleaning heads 400, 425, 450 and 475 to a motorized handle, such as described with reference to FIG. 8, below. Also the nodule polishing elements and curved squeegee elements described above can have any number of geometric shapes that include contoured or shaped walls, wiping edges and/or tips, such as described with reference to FIGS. 5A-F, 6A-6H and 7A-7G. Also, the prophy-cup polishing elements, the nodule polishing elements, the curved squeegee elements and the bristle tufts can protrude form the moving supports to any suitable height or combination of heights. Further, the wiping fins can have any number of different geometries that include shaped or contoured walls or tips, which are further described in application Ser. No. 10/454, 281, filed Jun. 3, 2003, and titled "MULTI-DIRECTIONAL WIPING ELEMENTS AND DEVICE USING THE SAME", referenced previously.

Figure 5A:
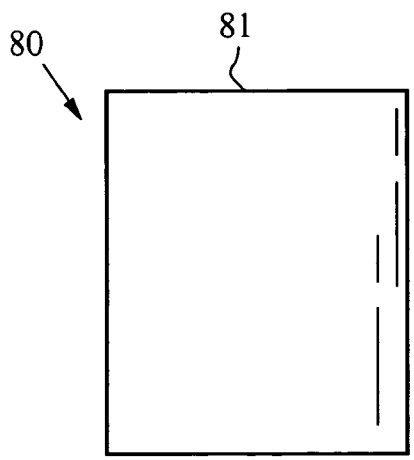
FIGS. 5A-F show several shaped or contoured squeegee edges, in accordance with the embodiments of the invention.
Figure 5B:
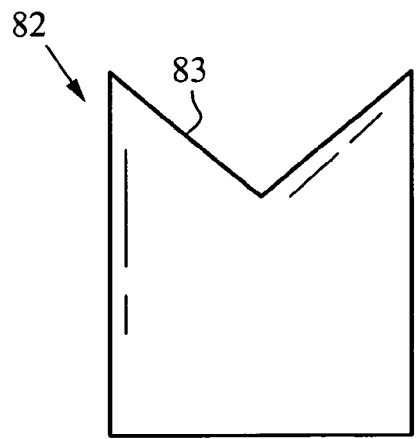
Figure 5C:
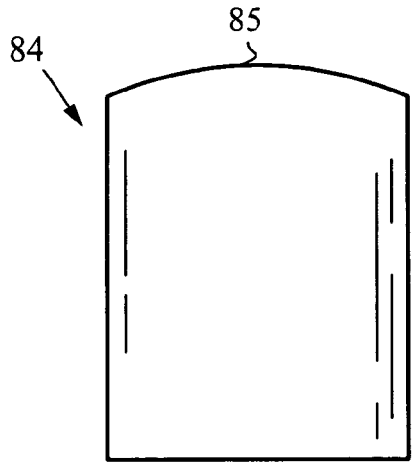
Figure 5D:
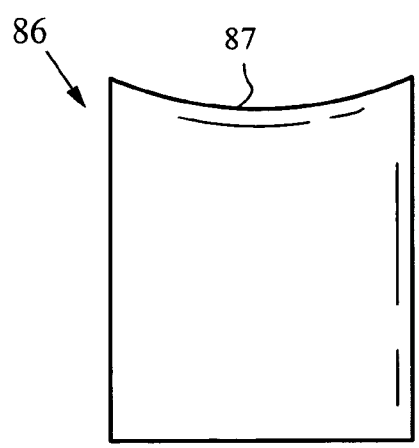
Figure 5E:
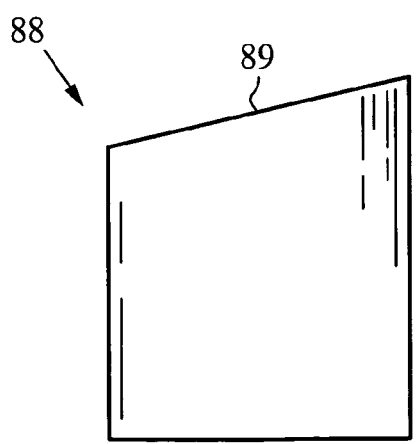
Figure 5F:
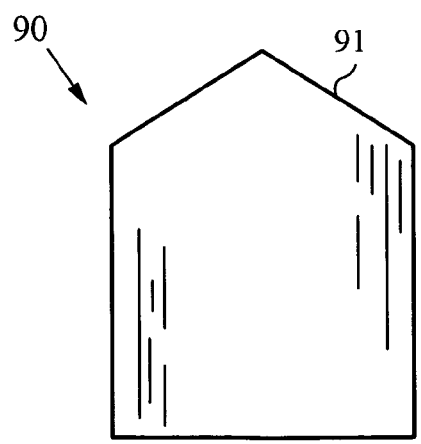

FIGS. 5A-F illustrate several shaped squeegee segments and/or partial structures of squeegee elements, used in the present invention. FIG. 5A shows a squeegee segment 80 with a planar contact edge 81; FIG. 5B shows a squeegee segment 82 with a V-shaped or notched contact edge 83; FIG. 5C shows a squeegee segment 84 with a convex contoured contact edge 85; FIG. 5D shows a squeegee segment 86 with a concave contoured contact edge 87; FIG. 5E shows a squeegee segment 88 with a diagonally contoured contact edge 89; and FIG. 5F shows a squeegee segment 90 with a pointed contact edge 91. The shaped squeegee segments described above can be combined in any number of ways to provide elongated squeegee wiping edges used in the oral cleaning device, system and method of the present invention.

FIGS. 6A-H illustrate several symmetrical nodule polishing element geometries that are useful in contact devices of the present invention. FIG. 6A shows a nodule 610 with cylindrical protruding walls 611 and a rounded tip portion 612; FIG. 6B shows a nodule 620 with cylindrical protruding walls 621 and a flat top 622; FIG. 6C shows a nodule 630 with contoured protruding walls 631 and a flat top 632; FIG. 6D shows a pointed nodule 640 with tapered protruding walls 641 and a tip 642; FIG. 6E shows a rectangular nodule 650 with planar walls 651 and a flat top 652; FIG. 6F shows a nodule 660 with planar walls 661 and a rounded tip portion 662; FIG. 6G shows a star shaped nodule 670 with protruding walls 671 and a star-shaped top 672; and FIG. 6H shows a triangular nodule 680 with protruding walls 681 and triangular-shaped top 682.

Figure 7A:
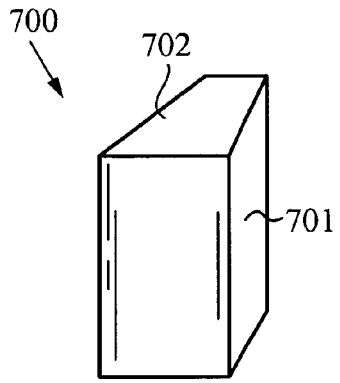
FIGS. 7A-G show alternative nodule polishing elements, in accordance with the embodiments of the invention.
Figure 7B:
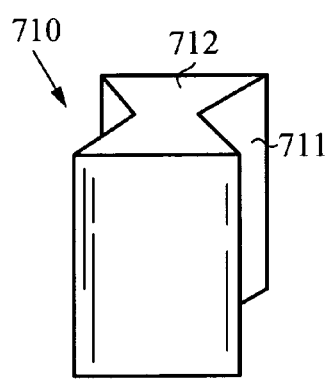
Figure 7C:
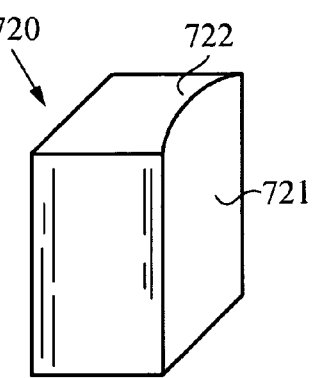
Figure 7D:
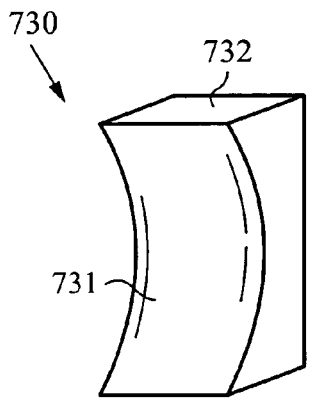
Figure 7E:
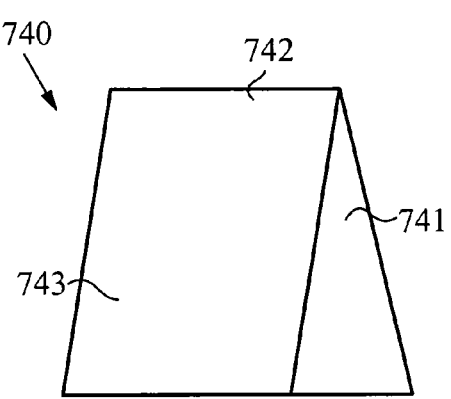
Figure 7F:
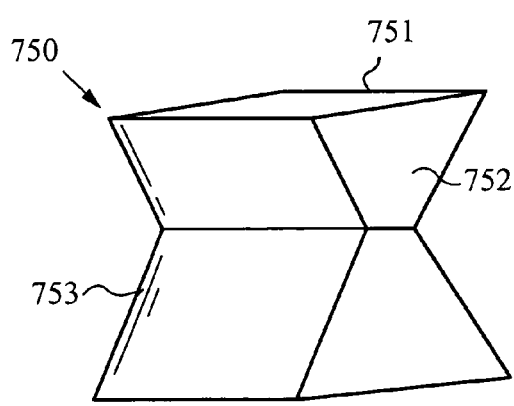
Figure 7G:
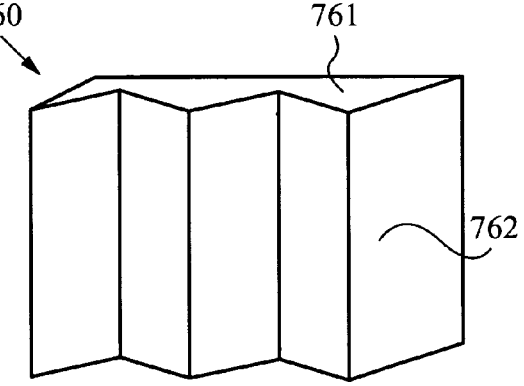

FIGS. 7A-G illustrate several asymmetrical nodule polishing element geometries that are useful in contact devices of the present invention. FIG. 7A shows a wedge-shaped nodule 700 with protruding walls 701 and a flat top 702; FIG. 7B shows a nodule 710 with contoured walls 711 and a bow-tie shaped flat top 712; FIG. 7C shows a curved nodule 720 with protruding walls 721 (curved in the elongation direction) and a flat top 722; FIG. 7D shows a curved nodule 730 with protruding walls 731 (curved in the protruding direction) and a flat top 732; FIG. 7E shows a wedge-shaped nodule 740 with tapered walls 743, triangular walls 741 and an edge 742; FIG. 7F shows a nodule 750 with angled walls 753, bow-tie shaped walls 752 and a flat top 751; and FIG. 7G shows a nodule 760 with contoured walls 762 and a flat top 761. It will be clear to one skilled in the art that any number of symmetric and asymmetric nodule geometries and combinations thereof are useful in the contact device of the present invention. Further descriptions of nodule structures and their applications are described in U.S. Pat. No. 6,865,767, titled "DEVICE WITH MULTI-STRUCTURAL CONTACT ELEMENTS", referenced previously.

Figure 8:
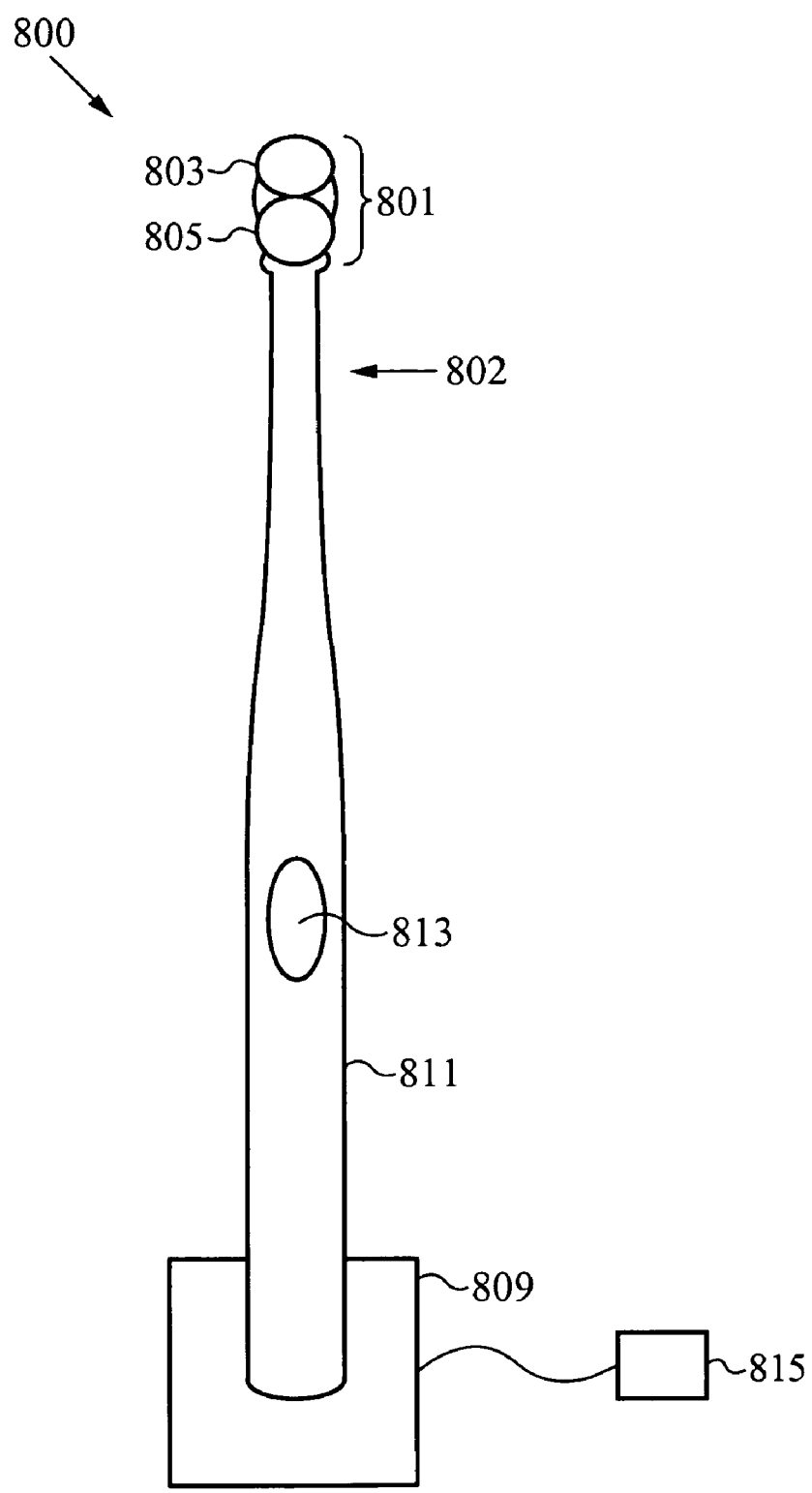
FIG. 8 shows a schematic representation of a motorized device comprising a motorized handle configured to vibrate, rotate and/or oscillate a cleaning head with at least one movable section with a polishing element, in accordance with the embodiments of the invention.

Now referring to FIG. 8, in accordance with the embodiments of the invention, an oral care system 800 comprises a toothbrush head 802 with a cleaning head 801. The cleaning head includes one or more movable sections 803 and 805 that rotate, oscillate, vibrate, move back and forth or any combination thereof. At least one of the movable section 803 and 805 include a prophy-cup polishing element, such described above with reference to FIGS. 1A-1F, 2A-2B, 3A-3B and 4A-4D. Preferably, at least one of the movable sections 803 and 805 also includes nodule polishing elements and/or bristle tufts. The system 800 comprises a handle section 811 which can include a power supply, such as a battery and/or can be configured to couple to an external power supply 815. The power supply drives mechanisms in the handle section 811 to cause one or more of the movable sections 803 and 805 to rotate, oscillate, vibrate or otherwise move. The handle portion 811 can include a switch 813 configured to start and stop the rotation, oscillation, vibration or other movement of one or more of the movable sections 803 and 805. Also, it will be clear to one skilled in the art that the toothbrush head 802 can be configured to be removable from the handle portion 811. In accordance with yet further embodiments of the invention the oral-care system 800 comprises a toothbrush head 802 with a polishing head 801 that includes a movable section 803 with a prophy-cup polishing element and a stationary section 805 with a squeegee polishing element, nodule polishing elements, bristle tufts, or a combination thereof.

The present invention provides an alternative dentition cleaning system and device to a brush-only system and device. Devices, in accordance with the embodiments of the invention, can be made to efficiently apply oral cleaning agents to teeth and gums and can be made to clean teeth and gums without requiring a high degree of technique or dexterity. Further, devices made in accordance with the embodiments of the invention can be less abrasive to both teeth and gums than a conventional bristle-only toothbrush.

It will be clear to one skilled in the art, from the description provided above, and the appended claims below, that the prophy-cup polishing elements, squeegee polishing elements, nodule polishing elements, bristle tufts and the features thereof can be combined in any number of different ways. Accordingly, the preceding preferred embodiment of the invention is set forth without any loss of generality to, and without imposing limitations upon, the claimed invention.

What is claimed is:

1. An oral-care device comprising a cleaning head, the cleaning head comprising a movable section comprising a prophy-cup polishing element and bristle tufts protruding therefrom, wherein the prophy-cup polishing element comprises squeegee segments with elongated walls that intersect with and extend outward from an outer wall of the prophy-cup polishing element to form intersecting top wiping edges and wiping fins with side wiping edges, wherein at least a portion of the bristle tufts surround prophy-cup polishing element.

2. The device of claim 1, wherein the prophy-cup polishing element surrounds at least a portion of the bristle tufts.

3. The device of claim 1, wherein at least a portion of the bristle tufts protrude to a height greater than a height of wiping edges of the prophy-cup polishing element.

4. The device of claim 1, wherein the cleaning head further comprises nodule polishing element.

5. The device of claim 1, further comprising a motorized handle configured to power the movable section.

6. The device of claim 1, further comprising a curved squeegee polishing element.

7. The device of claim 1, wherein wiping edges of the prophy-cup polishing element are contoured.

8. The device of claim 1, further comprising a squeegee segment protruding from the cleaning head.

9. The device of claim 8, wherein the prophy-cup polishing element includes the squeegee segment.

10. The device of claim 8, wherein walls of the prophy-cup polishing element are contoured.

11. An oral-care system comprising:
a) a plurality of movable sections each with polishing elements and bristles; and
b) a motorized handle with a power supply that drives mechanisms to automatically move each of the movable sections separately while the motorized handle is stationary, wherein at least one of the polishing elements is a prophy-cup polishing element with wiping fins that intersect with and extend outward from an outer wall of the prophy-cup polishing element to form intersecting top wiping edges and wiping fins with side wiping edges.

12. An oral-care device comprising a cleaning head, the cleaning head having a movable section with a prophy-cup polishing element and bristle tufts protruding therefrom, wherein the prophy-cup polishing element comprises squeegee segments with elongated walls that intersect with and extend outward from an outer wall of the prophy-cup polishing element to form intersecting top wiping edges and wiping fins with side wiping edges, wherein at least a portion of the bristle tufts protrude to a height greater than a height of wiping edges of the prophy-cup polishing element.

* * * * *